(12) United States Patent
Kim et al.

(10) Patent No.: US 7,326,804 B2
(45) Date of Patent: Feb. 5, 2008

(54) TRIETHYLENEGLYCOL ESTER BASED PLASTICIZER COMPOSITION FOR POLYVINYL CHLORIDE RESIN AND METHOD OF PREPARING THE SAME

(75) Inventors: Hyunkyu Kim, Daejeon (KR); Kyeseok Lee, Daejeon (KR); Kyu Il Lee, Daejeon (KR); Byoungkue Chun, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 11/402,600

(22) Filed: Apr. 12, 2006

(65) Prior Publication Data
US 2006/0229394 A1    Oct. 12, 2006

(30) Foreign Application Priority Data

Apr. 12, 2005  (KR)  ............ 10-2005-0030376
Mar. 10, 2006  (KR)  ............ 10-2006-0022714

(51) Int. Cl.
*C07C 69/00* (2006.01)
(52) U.S. Cl. ............ 560/129; 560/81; 560/90; 560/112; 524/239; 524/308; 526/344
(58) Field of Classification Search ............ 560/129, 560/81, 90, 112, 126; 524/239, 308; 526/344
See application file for complete search history.

(56) References Cited

U.S. PATENT DOCUMENTS 2,537,595 A * 1/1951 Levy et al. ............ 524/292

7,071,252 B2 * 7/2006 Stanhope et al. ............ 524/292

FOREIGN PATENT DOCUMENTS

| JP | 55037428 | 3/1980 |
|---|---|---|
| JP | 1113450 | 5/1989 |
| JP | 5155809 | 6/1993 |
| JP | 6127982 | 5/1994 |
| JP | 6271730 | 9/1994 |
| SU | 1694557 | 3/1989 |

OTHER PUBLICATIONS

Korean Intellectual Property Office, PCT International Search Report, Date of Mailing: Jul. 26, 2006.

* cited by examiner

*Primary Examiner*—Yvonne Eyler
*Assistant Examiner*—Sudhakar Katakam
(74) *Attorney, Agent, or Firm*—Cantor Colburn LLP

(57) ABSTRACT

Provided is a novel triethyleneglycol based compound, a plasticizer composition for polyvinyl chloride resin including the same, and a method of preparing the plasticizer composition. In particular, the plasticizer composition for polyvinyl chloride resin includes the novel compound, 2-(2-(2-(2-ethylhexanoyloxy)ethoxy)ethoxy)ethyl 2-ethylhexanoate, and 2-(2-(2-phenylcarbonyloxyethoxy)ethoxy)ethyl benzoate in a proper mixture ratio. A polyvinyl chloride prepared using the plasticizer composition has low heating loss, excellent adhesion, high plasticization efficiency, high elongation, high tensile strength, and high transparency.

5 Claims, No Drawings

TRIETHYLENEGLYCOL ESTER BASED PLASTICIZER COMPOSITION FOR POLYVINYL CHLORIDE RESIN AND METHOD OF PREPARING THE SAME

CROSS-REFERENCE TO RELATED PATENT APPLICATIONS

This application claims the benefit of Korean Patent Application No. 10-2005-0030376, filed on Apr. 12, 2005, and Korean Patent Application No. 10-2006-0022714, filed on Mar. 10, 2006, in the Korean Intellectual Property Office, the disclosure of which is incorporated herein in its entirety by reference.

BACKGROUND OF THE INVENTION

1. Field of the Invention

The present invention relates to a novel triethyleneglycol based compound and a plasticizer composition for polyvinyl chloride resin including the same, and more particularly, to a triethyleneglycol ester based plasticizer composition that is used to prepare a polyvinyl chloride resin having low heating loss, excellent adhesion, high plasticization efficiency, high elongation, high tensile strength, and high transparency.

2. Description of the Related Art

Polyvinyl chloride resins are homopolymers of vinyl chloride monomers or copolymers containing 50% or more of vinyl chloride, and are widely used resins preferably manufactured by extrusion molding, injection molding, calendaring, etc. Polyvinyl chloride resins are used in a wide range of applications, such as pipes, electric wires, electrical and mechanical products, toys, films, sheets, artificial leathers, tarpaulin, tapes, food packaging, and medical products, all of which can be manufactured using the methods described above. Polyvinyl chloride resins may have various properties depending on additives such as plasticizers, stabilizers, fillers, pigments, etc, added in a proper ratio thereto.

Plasticizers added to polyvinyl chloride resins are necessarily used to provide workability, flexibility, electric insulation, adhesiveness, etc. to the polyvinyl chloride resins. Examples of such plasticizers include phthalates, adipates, and trimellitates. In particular, phthalates, such as di-ethylhexyl phthalate (DEHP), di-butyl phthalate (DBP), di-isodecyl phthalate (DIDP), butyl benzyl phthalate (BBP), and di-isononyl phthalate (DINP), and adipates such as di-2-ethylhexyl adipate (DEHA) are commonly used.

Meanwhile, cling film, which is widely used in household applications, requires properties of elongation, adhesiveness, transparency, and low heating loss. In particular, since cling film is used in food packaging, transparency is required such that food packaged can be directly seen with naked eyes, elongation is required such that food can be well packed, and adhesiveness is required such that the cling film is not separated from food wrapped in the cling film. In addition, low heating loss is required to decrease the amount of gas generated during a manufacturing process and to increase the product yield.

As for a single-component triethyleneglycol ester, for example, an ester synthesized by reacting triethyleneglycol with only 2-ethylhexanoic acid as an aliphatic acid or a benzoic acid, its miscibility with respect to polyvinyl chloride resin decreases during cling film manufacturing processes. As a result, such a single component triethyleneglycol ester cannot be used as a plasticizer for a polyvinyl chloride resin, but is suitable for a lubricating oil and other use. When a single-component ester synthesizing by reacting neopentylglycol with 2-ethylhexanoic acid as an aliphatic acid is used, a polyvinyl chloride resin to which the plasticizer ester is add exhibits high hardness, low transparency, and low elongation; and when a single-component ester synthesizing by reacting triethyleneglycol with 2-ethylhexanoic acid is used, a polyvinyl chloride resin to which the plasticizer ester is added exhibits high workability but low elongation, low adhesion, and low transparency. In addition, even when a multi-component ester based plasticizer composition is used, a polyvinyl chloride resin to which the plasticizer composition is added may exhibit different properties according to the kind and composition of a carboxylic acid and alcohol used in the manufacturing process.

That is, it is difficult to obtain a polyvinyl chloride resin having desired properties in terms of heating loss, adhesiveness, and plasticization efficiency when the single-component or multi-component ester based plasticizer compositions described above are added to a polyvinyl chloride resin. Accordingly, there is a need to develop a multi-component ester based plasticizer composition to optimize the miscibility with respect to a polyvinyl chloride resin, elongation, adhesiveness, transparency and tensile strength.

SUMMARY OF THE INVENTION

The present invention provides a novel triethyleneglycol based compound.

The present invention also provides a plasticizer composition containing the novel triethyleneglycol based compound.

The present invention also provides a method of preparing the plasticizer composition.

The present invention also provides a polyvinyl chloride resin containing the plasticizer composition.

The present invention also provides a cling film used for food packaging including the plasticizer composition.

According to an aspect of the present invention, there is provided a triethyleneglycol based compound represented by formula 1:

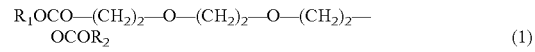

where $R_1$ is a C3-C12 alkyl group and $R_2$ is a C6-C10 aryl group.

According to another aspect of the present invention, there is provided a plasticizer composition including a compound represented by formula 1.

The plasticizer composition may further include a compound represented by formula 2 and a compound represented by formula 3:

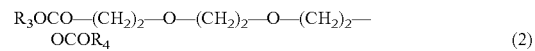

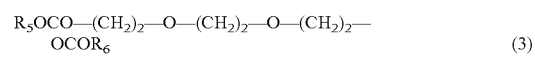

where $R_3$ and $R_4$ are each independently a C3-C12 alkyl group, and $R_5$ and $R_6$ are each independently C6-C10 aryl group.

According to still another aspect of the present invention, there is provided a method of preparing a plasticizer composition, the method including reacting a mixture of 10-40 wt % of triethyleneglycol, 1-80 wt % of C3-C12 aliphatic acid, 1-60 wt % of a C6-C10 aromatic acid, and 0.001-3 wt % of a catalyst.

According to yet another aspect of the present invention, there is provided a polyvinyl chloride resin including the plasticizer composition.

According to another aspect of the present invention, there is provided a wrap film that is used in food packaging, including the plasticizer composition.

DETAILED DESCRIPTION OF THE INVENTION

The present invention will now be described in detail by explaining embodiments of the invention A triethyleneglycol based compound according to an embodiment of the present invention is represented by formula 1:

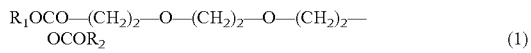
$$R_1OCO-(CH_2)_2-O-(CH_2)_2-O-(CH_2)_2-OCOR_2 \quad (1)$$

where $R_1$ is a C3-C12 alkyl group and $R_2$ is a C6-C10 aryl group.

The triethyleneglycol based compound represented by formula 1 can be prepared by reacting a mixture of 10-40 wt % of triethyleneglycol, 1-80 wt % of C3-C12 aliphatic acid, 1-60 wt % of a C6-C10 aromatic acid, and 0.001-3 wt % of a catalyst using a method that is well known to a person having ordinary skill in the art. The reactor may be a batch reactor, a mixed flow reactor, or a tubular reactor. However, the reactor is not limited thereto.

This reaction is known as esterification and may be performed at 100-300□ for 4-10 hours. When the reaction temperature is in the range of 100□-300□, the esterification product generated from the reaction does not decompose and a high reaction rate can be obtained. When the reaction time is in the range of 4-10 hours, a high conversion rate and high yield can be obtained and the desired product can be prepared at low costs.

The mixture may further include 1-10 wt % of an entrainer. The entrainer is an assistant substance that discharges $H_2O$ generated as a by-product of the esterification to the outside. The removal of the $H_2O$ generated contributes to a shift of the reaction equilibrium to the desired products because the reverse reaction of the esterification occurs less according to the Le Chatelier principle. Accordingly, use of the entrainer results in an increase of the yield of a desired product. The entrainer can be an organic solvent, such as n-hexane, toluene, xylene; or an inert gas such as nitrogen gas. Preferably, the entrainer can be toluene, xylene, or inert gas. However the entrainer is not limited to these materials described above.

The catalyst promotes the esterification. Examples of the catalyst include an acidic catalyst, such as sulfuric acid, hydrochloric acid, phosphoric acid, nitric acid, paratoluenesulfonic acid, methanesulfonic acid, alkyl sulfuric acid, or the like; a metal salt, such as aluminum lactate, lithium fluoride, potassium chloride, cesium chloride, calcium chloride, ferric chloride, aluminum phosphate, or the like; a metal oxide, such as heteropoly acid, or the like; natural/synthesis zeolite; cationic and anionic exchange resin; and an organic metal, such as tetraalkyltitanate, a polymer thereof, or the like. For example, the catalyst can be a paratoluenesulfonic acid or a tetraisopropyltitanate. However, the catalyst is not limited thereto.

The post treatment required after the esterification is completed is not limited. For example, an unreacted reactant material is removed through vacuum distillation, and then a neutralizing reaction is performed using a base solution, such as a NaOH aqueous solution. Then, the neutralization product is washed using water and selectively dehydrated under reduced pressure, and then an adsorbent is added thereto and then filtered. As a result, a plasticizer composition can be obtained. However, the post treatment is not limited thereto.

Meanwhile, the reaction product obtained using the processes described above include, in addition to the compound of formula 1, compounds of formula 2 and formula 3:

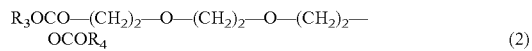
$$R_3OCO-(CH_2)_2-O-(CH_2)_2-O-(CH_2)_2-OCOR_4 \quad (2)$$

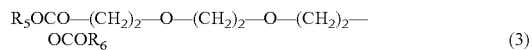
$$R_5OCO-(CH_2)_2-O-(CH_2)_2-O-(CH_2)_2-OCOR_6 \quad (3)$$

where $R_3$ and $R_4$ are each independently a C3-C12 alkyl group, and $R_5$ and $R_6$ are each independently a C6-C10 aryl group.

Accordingly, in order to obtain only the compound of formula 1, the compound of formula 1 should be separated from the reaction product containing the compounds of formulae 1 through 3. The separation method can be any method that is well known in the art, and is not limited.

For example, the compound of formula 1 can be separated using column chromatography. An adsorbent used as a stationary phase can be $Al_2O_3$, $SiO_2$, charcoal, $MgSiO_2$, or the like, all of which are well known in the art. In particular, the adsorbent can be a silica gel. However, the adsorbent is not limited to these materials. A mobile phase can be an organic solvent, such as n-hexane, ethylacetate, chloroform, or toluene, which is well known in the art. For example, the mobile phase is n-hexane or ethylacetate. However, the mobile phase is not limited to these materials described above. Although the kind of a mobile phase varies according to polarities of a mixture to be separated and a stationary phase, in general, a mobile phase having a proper polarity obtained by mixing a mobile phase having high polarity and a mobile phase having low polarity in a proper mixture ratio is used.

In the compound of formula 1, $R_1$ may be a 1-ethyl pentyl group, and $R_2$ may be a phenyl group. However, $R_1$ and $R_2$ are not limited thereto.

A plasticizer composition according to an embodiment of the present invention includes the compound of formula 1. Inventors of the present invention found that a polyvinyl chloride product prepared using a plasticizer composition containing the compound of formula 1 exhibits lower heating loss, excellent adhesion, and higher plasticization efficiency than a polyvinyl chloride product prepared using a conventional plasticizer composition.

A plasticizer composition containing the compound of formula 1 can be prepared using any method that is well known to a person having ordinary skill in the art by adding the compound of formula 1. The amount of the compound of formula 1 may be in the range of 0.1 wt %-99.5 wt %, preferably 5 wt %-85 wt %, more preferably 15 wt %-70 wt %, and most preferably 30 wt %-60 wt %, based on the entire amount of the plasticizer composition. When the compound of formula 1 is less than 0.1 wt % based on the entire amount of the plasticizer composition, the excellent physical properties of the composition obtainable by containing the compound of formula 1, such as low heating loss, high adhesion, and high plasticization efficiency cannot be obtained. On the other hand, when the compound of formula 1 is more than 99.5 wt % based on the entire amount of the plasticizer composition, thermal stability, migration resistance, and adhesiveness of a polyvinyl chloride product to which the plasticizer composition is added decrease. In the plasticizer composition including the compound of formula 1, $R_1$ may be 1-ethyl pentyl group and $R_2$ may be a phenyl group. However, $R_1$ and $R_2$ are not limited thereto.

A plasticizer composition according to another embodiment of the present invention may further include triethyleneglycol esters represented by formulae 2 and 3:

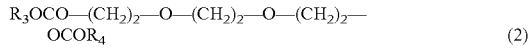

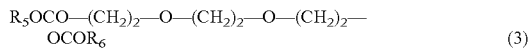

where $R_3$ and $R_4$ are each independently a C3-C12 alkyl group, and $R_5$ and $R_6$ are each independently a C6-C10 aryl group.

A polyvinyl chloride product prepared using a plasticizer composition containing the triethyleneglycol esters of formulae 2 and 3 exhibits lower heating loss, excellent adhesion, and higher plasticization efficiency than a polyvinyl chloride product prepared using a conventional plasticizer composition.

The compounds of formulae 2 and 3 can be prepared using the method of preparing the compound of formula 1.

The plasticizer composition containing the compounds of formulae 2 and 3 can be prepared using any method that is well known to a person having ordinary skill in the art. However, the preparing method is not limited. The amount of the compounds of formulae 1 through 3 may be in the range of 0.1 wt %-99.5 wt %, preferably 5 wt %-85 wt %, more preferably 15 wt %-70 wt %, and most preferably 30 wt %-60 wt %, based on the entire amount of the plasticizer composition. When the amount of the compounds of formulae 1 through 3 is less than 0.1 wt % of the plasticizer composition, the physical properties, such as high adhesion, high plasticization efficiency, and high elongation, of the composition obtainable by containing the compounds of formulae 1 through 3 cannot be obtained. On the other hand, when the amount of the compounds of formulae 1 through 3 is greater than 99.5 wt % of the plasticizer composition, a polyvinyl chloride product to which the plasticizer composition is added exhibits low thermal stability, low migration resistance, and lower heating loss.

In formulae 1 through 3, $R_1$ $R_3$, and $R_4$ may be a C4-C10 alkyl group. However, $R_1$ $R_3$, or $R_4$ is not limited thereto.

A plasticizer composition according to an embodiment of the present invention includes (a) 10-80 wt % of the compound of formula 1, (b) 10-80 wt % of the compound of formula 2, and (c) 0-60 wt % of the compound of formula 3.

When the amount of the compound of formula 1 is less than 10 wt %, a polyvinyl chloride product to which the plasticizer composition is added has high heating loss, low adhesiveness, and low plasticization efficiency. On the other hand, when the amount of the compound of formula 1 is greater than 80 wt %, a polyvinyl chloride product to which the plasticizer composition is added has low thermal stability, low migration resistance, and low adhesiveness. When the amount of the compound of formula 2 is less than 10 wt %, a polyvinyl chloride product to which the plasticizer composition is added has low adhesiveness, low plasticization efficiency, and low elongation. On the other hand, when the amount of the compound of formula 2 is greater than 80 wt %, a polyvinyl chloride product to which the plasticizer composition is added has low thermal stability, low migration resistance, and high heating loss. When the amount of the compound of formula 3 is greater than 60 wt %, the plasticization efficiency of a polyvinyl chloride product to which the plasticizer composition is added decreases significantly and the liquid phase is crystallized to be hardened.

In the plasticizer composition according to the current embodiment, the amount of the compound of formula 1 can be in the range of 20-65 wt %, and preferably 30-55 wt %; the amount of the compound of formula 2 can be 20-65 wt %, and preferably 30-55 wt %; and the amount of the compound of formula 3 can be in the range of 1-40 wt %, and preferably 5-20 wt %.

The plasticizer composition described above can be prepared by reacting a mixture of (i) 10-40 wt % of triethyleneglycol, (ii) 1-80 wt % of C3-C12 aliphatic acid, (iii) 1-60 wt % of C6-C10 aromatic acid, and (iv) 0.001-3 wt % of a catalyst using a method that is known to a person having ordinary skill in the art. The reactor may be a batch reactor, a mixed flow reactor, or a tubular reactor. However, the reactor is not limited thereto.

When the amounts of the triethyleneglycol, the aliphatic acid, and the aromatic acid are outside these ranges, it is difficult to prepare a plasticizer composition having a desired mixture ratio. When the amount of the catalyst is less than 0.001 wt %, a reaction catalyzing effect does not occur. On the other hand, when the amount of the catalyst is greater than 3 wt %, the reactant solution becomes discolored.

This reaction is an esterification process, and may be performed at 100-300° C. for 4-10 hours. When the reaction temperature is less than 100° C., the reaction occurs very slowly so that the reaction product is inefficiently produced. On the other hand, when the reaction temperature is higher than 300° C., the reaction product decomposes and is discolored. When the reaction time is less than 4 hours, an insufficient reaction occurs, and thus, the conversion is low and the product yield is small. On the other hand, when the reaction time is greater than 10 hours, the reaction almost reaches an equilibrium conversion rate and thus further reaction hardly takes place.

The reaction mixture may further include 1-10 wt % of entrainer. The entrainer can be an organic solvent, such as n-hexane, toluene, xylene; or an inert gas such as nitrogen gas. Preferably, the entrainer can be n-hexane, toluene, xylene, or inert gas. However the entrainer is not limited to these materials described above.

The catalyst promotes the esterification reaction. Examples of the catalyst include an acidic catalyst, such as sulfuric acid, hydrochloric acid, phosphoric acid, nitric acid, paratoluenesulfonic acid, methanesulfonic acid, alkyl sulfuric acid, or the like; a metal salt, such as aluminum lactate, lithium fluoride, potassium chloride, cesium chloride, calcium chloride, ferric chloride, aluminum phosphorate, or the like; a metal oxide, such as heteropoly acid, or the like; natural/synthesis zeolite; cationic and anionic exchange resin; and an organic metal, such as tetra alkyl titanate, a polymer thereof, or the like. For example, the catalyst can be a paratoluenesulfonic acid or a tetraisopropyltitanate. However, the catalyst is not limited thereto.

The post treatment required after the completion of the esterification reaction is not limited. For example, an unreacted reactant material is removed through vacuum distillation, and then a neutralizing reaction is performed using a base solution, such as a NaOH aqueous solution. Then the neutralization product is washed using water and selectively dehydrated under reduced pressure, and then an adsorbent is added thereto and then filtered. As a result, a plasticizer composition can be obtained. However, the post treatment is not limited thereto.

A polyvinyl chloride resin using the plasticizer composition of the present invention as a plasticizer according to an embodiment of the present invention exhibits low heating loss, excellent adhesiveness, and high plasticization efficiency. A method of preparing a polyvinyl chloride resin using the plasticizer composition as a plasticizer is not limited, and any method that is well known in the art can be used.

The present invention will be described in further detail with reference to the following examples. These examples are for illustrative purposes only and are not intended to limit the scope of the present invention. Properties of samples prepared according to Examples and Comparative Examples were measured in the following manner.

Tensile Strength and Elongation

Based on ASTM, D412UTM was used to measure a tensile strength and elongation. Setting a cross head speed at 200 mm/min, a break point of the sample was used for measurement. Tensile strength and elongation were calculated using Equations 1 and 2.

Tensile Strength $(kg_f/mm^2)$=Load $(kg_f)$/{Thickness (mm)×Width (mm)}  [Equation 1]

Elongation (%)={Length after being extended/initial length}×100  [Equation 2]

Hardness

Hardness was measured to qualify plasticization efficiency. Based on ASTM D2240, a needle of a hardness tester (A type) was completely contacted to one site of a sample and after 5 minutes a hardness value was read. Five sites of respective samples were measured and their respective average values were obtained. The hardness was measured directly after the sample preparation and one day after the sample preparation.

Transparency

Two methods were used. In the first method, a haze value of a sample was measured using a haze meter directly after the sample preparation. In the second method, a cling film sample was manufactured, and after 7 days the cling film sample was measured with naked eyes to compare a cling film sample prepared using a di-2-ethylhexyladipate (DEHA) that is a standard plasticizer. The results are estimated as 'better', 'equal', and 'worse'. The expression of 'better' indicates that the cling film sample exhibits better transparency than the cling film sample prepared using the standard plasticizer. The expression of 'equal' indicates that the cling film sample exhibits the equivalent transparency as the cling film sample prepared using the standard plasticizer. The expression of 'worse' indicates that the cling film sample exhibits worse transparency than the cling film sample prepared using the standard plasticizer.

Adhesiveness

A sample was directly contacted with hands and compared with a cling film sample prepared using DEHA. The results are shown on a 5-point scale: better adhesion (5), similar adhesion (3), and poorer adhesion (1).

EXAMPLE 1

Preparation of Triethyleneglycol Ester Based Plasticizer Composition 2.5 mol of triethyleneglycol, 5.25 mol of 2-ethylhexanoic acid, 2.25 mol of benzoic acid, 60 g of xylene as an entrainer, and 1.5 g of tetraisopropyltitanate as a catalyst were added to a 2L 4-neck round flask having a stirrer and a condenser, the temperature was increased to 220° C., and then the mixture was reacted for 6 hours.

Then, the flask was depressurized to a pressure of 1 mmHg at 220° C. using a vacuum pump to remove an un-reacted acid, and then a neutralizing reaction was performed using 10 wt % NaOH aqueous solution. The neutralization product was washed using water and dehydrated, and an adsorbent was added thereto and filtered. As a result, a triethyleneglycol ester mixture was obtained.

The obtained triethyleneglycol ester mixture was analyzed, and the composition was found to be 45 wt % of 2-(2-(2-(2-ethylhexanoyloxy)ethoxy)ethoxy)ethyl 2-ethylhexanoate, 45 wt % of 2-(2-(2-phenylcarbonyloxyethoxy)ethoxy)ethyl 2-ethylhexanoate, and 9 wt % of 2-(2-(2-phenylcarbonyloxyethoxy)ethoxy)ethylbenzoate were obtained.

Preparation of Polyvinyl Chloride Resin

In order to measure a performance of the obtained triethyleneglycol ester mixture as a plasticizer, a sample was prepared based on ASTM D638. That is, 100 parts by weight of polyvinyl chloride (produced by LG Chemical Co., product name: LS100S) was blended with 36 parts by weight of the obtained triethyleneglycol ester mixture as a plasticizer, 14 parts by weight of an epoxy soybean oil (produced by Shindongbang Co.), 2 parts by weight of KA-901 produced by Japanese Rinken Vitamin Co. as a glycol based antifogging agent, and 1.2 parts by weight of LTX-630P produced by Korea Daehyup Co., Ltd. as a Ca—Zn organic composite stabilizer, and then the resultant mixture was processed to form a 5 mm-thick sheet using a roll mill at 175° C. for 3 minutes. Then, the obtained sheet was preheated at 185° C. for 3 minutes, heated for 3 minutes, and then cooled for 3 minutes, using a pressing device, thereby forming a 1 mm-thick sheet.

Subsequently, dumbbell-shaped samples of C type were prepared from the 1 mm sheet. The antifogging agent is an additive that prevents condensation of water vapor or the like on a cling film surface and thereby formation of haze thereby.

Results of the tests described above are shown in Table 2. In particular, the heating loss was measured in the following manner. First, the mixture was processed to prepare a 0.8 mm-thick sheet using a roll mill at 165° C. for 3 minutes. Then, 60 g of the 0.8 mm-thick sheet was processed to prepare a 0.4 mm-thick sample using a roll mill at 185° C. for 10 minutes. After 24 hours, the weight of the sample was measured and the heating loss was measured using Equation 3.

Heating loss (wt %)={1−(weight of sample being processed at 185° C. for 10 minutes)/60g}×100  [Equation 3]

EXAMPLE 2

A triethyleneglycol ester based plasticizer composition was prepared in the same manner as in Example 1, except that amounts of the reactant materials used were changed as shown in Table 1. The obtained triethyleneglycol ester mixture was analyzed and the composition was found to be 30 wt % of 2-(2-(2-(2-ethylhexanoyloxy)ethoxy)ethoxy)ethyl 2-ethylhexanoate, 52 wt % of 2-(2-(2-phenylcarbonyloxyethoxy)ethoxy)ethyl 2-ethylhexanoate, and 18 wt % of 2-(2-(2-phenylcarbonyloxyethoxy)ethoxy)ethylbenzoate were obtained.

Then a sample was prepared using the triethyleneglycol ester based plasticizer composition obtained above in the same manner as in Example 1. The same test as in Example 1 was performed on the prepared sample. The results are shown in Table 2.

EXAMPLE 3

A triethyleneglycol ester based plasticizer composition was prepared in the same manner as in Example 1, except that amounts of the reactant materials used were changed as shown in Table 1. The obtained triethyleneglycol ester mixture was analyzed and the composition was found to be 82 wt % of 2-(2-(2-(2-ethylhexanoyloxy)ethoxy)ethoxy)ethyl 2-ethylhexanoate, 15 wt % of 2-(2-(2-phenylcarbonyloxyethoxy)ethoxy)ethyl 2-ethylhexanoate, and 1 wt % of 2-(2-(2-phenylcarbonyloxyethoxy)ethoxy)ethylbenzoate were obtained.

Then, a sample was prepared using the triethyleneglycol ester based plasticizer composition in the same manner as in Example 1. The same test as in Example 1 was performed on the prepared sample. The results are shown in Table 2.

COMPARATIVE EXAMPLE 1

A sample was prepared in the same manner as in Example 1, except that di-2-ethylhexyladipate (produced by LG Chemical Co., Ltd., product name: DOA), which is most commonly used to form cling film, was used as a plasticizer. The same test as in Example 1 was performed on the prepared sample. The results are shown in Table 2.

COMPARATIVE EXAMPLE 2

A sample was prepared in the same manner as in Example 1, except that diisononyladipate (produced by LG Chemical Co., Ltd., product name: DINA), which is commonly used to form cling film, was used as a plasticizer. The same test as in Example 1 was performed on the prepared sample. The results are shown in Table 2.

COMPARATIVE EXAMPLE 3

A sample was prepared in the same manner as in Example 1, except that LGflex EBNW (produced by LG Chemical Co., Ltd.), which is an environmentally friendly plasticizer used in food packaging, was used as a plasticizer. The same test as in Example 1 was performed on the prepared sample. The results are shown in Table 2.

COMPARATIVE EXAMPLE 4

A sample was prepared in the same manner as in Example 1, except that acetylmonoglyceride (produced by II Shin Petrochemistry Co., Ltd, product name: SOLFA-AM-GT90) was used as a plasticizer. The same test as in Example 1 was performed on the prepared sample. The results are shown in Table 2.

TABLE 1

| | | Example 1 | Example 2 | Example 3 |
|---|---|---|---|---|
| Reactant Materials | triethyleneglycol (mol) | 2.50 | 2.50 | 2.53 |
| | 2-ethylhexanoic acid (mol) | 5.25 | 3.75 | 7.00 |
| | benzoic acid (mol) | 2.25 | 2.75 | 0.50 |
| | xylene (g) | 60 | 60 | 60 |
| | tetraisopropyltitanate (g) | 1.5 | 1.5 | 1.5 |

TABLE 2

| Section | | Example 1 | Example 2 | Example 3 | Comparative Example 1 | Comparative Example 2 | Comparative Example 3 | Comparative Example 4 |
|---|---|---|---|---|---|---|---|---|
| Tensile Strength ($kg_f/mm^2$) | | 2.13 | 2.20 | 2.05 | 1.87 | 2.01 | 2.02 | 2.10 |
| Elongation (%) | | 414 | 413 | 389 | 387 | 421 | 354 | 413 |
| Heating Loss (wt %) | | 1.66 | 1.30 | 1.26 | 2.81 | 1.58 | 4.21 | 4.17 |
| Hardness | Initial | 77.5 | 77.4 | 77.4 | 77.5 | 79.5 | 77.3 | 78.9 |
| | after one day | 80.6 | 80.0 | 81.0 | 80.5 | 82.1 | 80.4 | 82.3 |
| Transparency | Initial | 13.7 | 15.6 | 15.1 | 10.7 | 11.8 | 22.1 | 13.5 |
| | after 7 days | better | equal | equal | reference | equal | equal | equal |
| Adhesiveness | | 5 | 4 | 2 | 3 | 2 | 3 | 2 |

As shown in Table 2, the samples prepared using a plasticizer composition according to an embodiment of the present invention prepared according to Examples 1 through 3 exhibited lower heating loss, excellent adhesion, higher transparency, and higher elongation than the samples prepared according to Comparative Examples 1, 3, and 4. In addition, when compared with the sample prepared according to Comparative Example 2, the samples prepared according to Examples 1 through 3 exhibited lower heating loss and excellent adhesiveness.

A polyvinyl chloride resin prepared using a triethyleneglycol ester based plasticizer composition according to the present invention as a plasticizer has lower heating loss, excellent adhesion, high plasticization efficiency, high elongation, high tensile strength, and high transparency.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A plasticizer composition comprising:
   20-65 wt% of a compound represented by formula 1,
   20-65 wt% a compound represented by formula 2, and
   1-40 wt% of a compound represented by formula 3:

$$R_1OCO-(CH_2)_2-O-(CH_2)_2-O-(CH_2)_2-OCOR_2 \quad (1)$$

$$R_3OCO-(CH_2)_2-O-(CH_2)_2-O-(CH_2)_2-OCOR_4 \quad (2)$$

$$R_5OCO-(CH_2)_2-O-(CH_2)_2-O-(CH_2)_2-OCOR_6 \quad (3)$$

where $R_1$ is a C3-C12 alkyl group, $R_2$ is a C6-C10 aryl group, $R_3$ and $R_4$ are each independently a C3-C12 alkyl group, and $R_5$ and $R_6$ are each independently a C6-C10 aryl group.

2. The plasticizer composition of claim 1, wherein $R_1$ is a 1-ethyl pentyl group and $R_2$ is a phenyl group.

3. The plasticizer composition of claim 1, wherein the alkyl group of $R_1$, $R_3$, or $R_4$ has four carbon atoms through ten carbon atoms.

4. A polyvinyl chloride resin comprising the plasticizer composition of claim 1.

5. A cling film for food packaging, comprising the plasticizer composition of claim 1.